United States Patent [19]

Bühler et al.

[11] 4,325,870
[45] Apr. 20, 1982

[54] PROCESS FOR THE PREPARATION OF 2,6-DIAMINOPYRIDINE-AZO DYESTUFFS AND OF THEIR PRECURSORS

[75] Inventors: Ulrich Bühler, Schöneck; Ernst Heinrich, Neu-Isenburg, both of Fed. Rep. of Germany

[73] Assignee: Cassella Aktiengesellschaft, Frankfurt, Fed. Rep. of Germany

[21] Appl. No.: 136,814

[22] Filed: Apr. 2, 1980

[30] Foreign Application Priority Data

Apr. 23, 1979 [DE] Fed. Rep. of Germany ....... 2916319

[51] Int. Cl.³ ..................... C09B 29/42; C07D 213/74
[52] U.S. Cl. .................................... 260/156; 546/287; 546/289; 546/294; 546/307; 546/345
[58] Field of Search ............... 546/307, 345, 294, 287, 546/289; 260/156

[56] References Cited

U.S. PATENT DOCUMENTS 2,742,478  4/1956  Bavley et al. ................. 546/345
3,980,659  9/1976  Fleckenstein et al. ......... 546/307
4,225,716  9/1980  Buhler et al. .................. 546/286

*Primary Examiner*—Alan L. Rotman
*Attorney, Agent, or Firm*—Connolly and Hutz

[57] ABSTRACT

An improved process for producing 2,6-diaminopyridines and azo dyestuffs therefrom involves reacting a 2,6-dihalopyridine with a primary amine in a two-phase system of water and an insoluble or sparingly soluble inert organic solvent in the presence of an inorganic base.

7 Claims, No Drawings

PROCESS FOR THE PREPARATION OF 2,6-DIAMINOPYRIDINE-AZO DYESTUFFS AND OF THEIR PRECURSORS

The invention relates to a process for the preparation of compounds of the general formula I

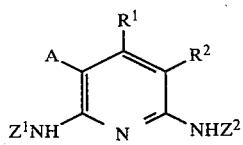

wherein A denotes hydrogen or a radical of the formula —N=N—D, $R^1$ denotes H, alkyl with 1 to 8 C atoms or optionally substituted phenyl, $R^2$ denotes H, cyano, nitro, acyl with 2 to 4 C atoms or sulphomethyl, $Z^1$ and $Z^2$ are identical or different and denote H, optionally substituted alkyl or polyalkoxyalkyl with in each case a total of 1 to 8 C atoms, cycloalkyl with 5 to 7 C atoms, alkenyl with 3 to 5 C atoms or optionally substituted phenyl and D denotes the radical of a customary diazo component of the aromatic or hetero-aromatic series, starting from compounds of the general formula II

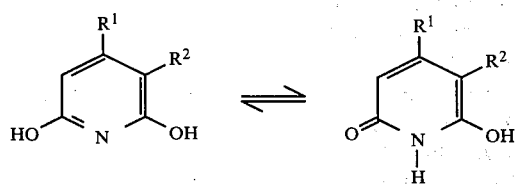

in which $R^1$ and $R^2$ have the abovementioned meanings.

Examples of possible substituents for $R^1$ are the following: methyl, ethyl, n-propyl, i-propyl, n-butyl, i-butyl, n-hexyl, β-ethylhexyl, phenyl, methoxyphenyl, methylphenyl, chlorophenyl and bromophenyl; examples of acyl radicals which $R^2$ can represent are formyl, acetyl, propionyl, n-butyryl and isobutyryl. Preferred substituents for $R^1$ are methyl, ethyl and n-propyl, and for $R^2$ cyano.

Alkyl radicals which $Z^1$ and/or $Z^2$ can represent have 1 to 8 C atoms, such as, for example, the radicals methyl, ethyl, propyl, n-, iso-, sec.- or tert.-butyl, pentyl, isopentyl, hexyl, heptyl, octyl and isooctyl, such as, for example, 2-ethylhexyl. Polyalkoxyalkyl radicals which $Z^1$ and/or $Z^2$ can represent are alkyl radicals with a total of 8 C atoms, the carbon chain of which is interrupted by 1 to 3 oxygen atoms. Both the alkyl radicals and the polyalkoxyalkyl radicals can be substituted by hydroxyl, alkoxy with 1 to 4 C atoms, alkenyloxy with 3 to 5 C atoms, cycloalkyloxy with 5 to 7 C atoms, phenoxy, phenylalkoxy, such as benzyloxy or phenethyloxy, acyloxy with 1 to 4 C atoms, cyano, —NH₂ or alkylamino or dialkylamino with a total of 2 to 8 C atoms.

Phenyl radicals which $Z^1$ and/or $Z^2$ represent can be substituted by alkoxy with 1 to 4 C atoms, hydroxyethoxy, alkyl with 1 to 4 C atoms, halogen, in particular fluorine, chlorine and bromine, or alkoxycarbonyl with 2 to 9 C atoms.

Customary diazo components D belong to the benzene, azobenzene, benzophenone, diphenyl sulphone, thiazole, isothiazole, benzthiazole, benzisothiazole or thiadiazole series.

Known examples of amines from which the radicals D can be derived are aniline, o-, m- or p-toluidine, o-, m- or p-nitroaniline, o-, m- or p-cyanoaniline, 2,4-dicyanoaniline, o-, m- or p-chloroaniline, o-, m- or p-bromoaniline, 2,4,6-tribromoaniline, 2-chloro-4-nitroaniline, 2-bromo-4-nitroaniline, 2-cyano-4-nitroaniline, 2-methylsulphonyl-4-nitroaniline, 2-methyl-4-nitroaniline, 2-methoxy-4-nitroaniline, 4-chloro-2-nitroaniline, 4-methyl-2-nitroaniline, 4-methoxy-2-nitroaniline, 1-amino-2-trifluoromethyl-4-chlorobenzene, 2-chloro-5-aminobenzonitrile, 2-amino-5-chlorobenzonitrile, 1-amino-2-nitrobenzene-4-sulphonic acid n-butylamide or β-methoxyethylamide, 2,4-dinitroaniline, 2,4-dinitro-6-chloroaniline, 2,4-dinitro-6-bromoaniline, 2,4-dinitro-6-cyanoaniline, 1-amino-2,4-dinitrophen-6-yl methyl sulphone, 2,6-dichloro-4-nitroaniline, 2,6-dibromo-4-nitro-aniline, 2-chloro-6-bromo-4-nitroaniline, 2,6-dicyano-4-nitroaniline, 2-cyano-4-nitro-6-chloroaniline, 2-cyano-4-nitro-6-bromoaniline, 1-aminophen-4-yl methyl sulphone, 1-amino-2,6-dibromo-phen-4-yl methyl sulphone, 1-amino-2,6-dichlorophen-4-yl methyl sulphone, 1-amino-2,4-dinitrobenzene-6-carboxylic acid methyl ester or β-methoxyethyl ester, 3,5-dichloroanthranilic acid propyl ester, 3,5-dibromoanthranilic acid β-methoxyethyl ester, N-acetyl-p-phenylenediamine, 4-aminoacetophenone, 4-aminoazobenzene, 2',3-dimethyl-4-aminoazobenzene, 3',2-dimethyl-4-aminoazobenzene, 2,5-dimethyl-4-aminoazobenzene, 2-methyl-5-methoxy-4-aminoazobenzene, 2-methyl-4',5-dimethoxy-4-aminoazobenzene, 4'-chloro-2-methyl-5-methoxy-4-aminoazobenzene, 4'-nitro-2-methyl-5-methoxy-4-aminoazobenzene, 4'-chloro-2-methyl-4-aminoazobenzene, 2,5-dimethoxy-4-aminoazobenzene, 4'-chloro-2,5-dimethoxy-4-aminoazobenzene, 4'-nitro-2,5-dimethoxy-4-aminoazobenzene, 4'-chloro-2,5-dimethyl-4-aminoazobenzene, 4'-methoxy-2,5-dimethyl-4-aminoazobenzene, 4'-nitro-4-aminoazobenzene, 3,5-dibromo-4-aminoazobenzene, 2,3'-dichloro-4-aminoazobenzene, 3-methoxy-4-aminoazobenzene, 2-, 3- or 4-amino-benzophenone, 2-, 3- or 4-aminodiphenyl sulphone, 2-, 3- or 4-amino-benzoic acid methyl ester, ethyl ester, propyl ester, butyl ester, isobutyl ester, β-methoxy-ethyl ester, β-ethoxy-ethyl ester, methyl-diglycol ester, ethyl-diglycol ester, methyl-triglycol ester, ethyltriglycol ester, β-hydroxyethyl ester, β-acetoxy-ethyl ester, β-(β'-hydroxy-ethoxy)-ethyl ester, β-hydroxy-propyl ester, γ-hydroxy-propyl ester, ω-hydroxy-butyl ester and ω-hydroxy-hexyl ester, 5-nitroanthranilic acid methyl ester, isobutyl ester, methyldiglycol ester, β-methoxy-ethyl ester, β-butoxy-ethyl ester and β-acetoxy-ethyl ester, the dimethyl ester, diethyl ester, dipropyl ester and dibutyl ester of 3- or 4-aminophthalic acid, 5-aminoisophthalic acid or amino-terephthalic acid, 3- or 4-aminobenzoic acid amide, methylamide, propylamide, butylamide, isobutylamide, cyclohexylamide, β-ethyl-hexylamide, γ-methoxy-propylamide and γ-ethoxy-propylamide, 2-, 3- or 4-aminobenzoic acid dimethylamide, diethylamide, pyrrolidide, morpholide and N-methyl-N-β-hydroxyethylamide, 5-amino-isophthalic acid diamide and bis-γ-methoxy-propylamide, aminoterephthalic acid bis-diethylamide, 3- or 4-amino-phthalic acid imide, β-hydroxy-ethylimide and γ-hydroxypropylamide, 3-amino-6-nitro-phthalic acid β-hydroxy-ethylimide, 2-, 3- or 4-aminobenzenesulphonic acid dimethylamide, diethylamide, pyrrolidide and morpholide, methylsulphonic acid 2'-, 3'- or 4'-amino-phenyl ester, ethylsulphonic acid 2'-, 3'- or 4'-amino-phenyl ester, butylsulphonic acid 2'-, 3'- or 4'-aminophenyl ester, benzenesulphonic acid 2'-, 3'- or 4'-aminophenyl ester, 4-aminonaphthalic acid ethylimide, butylimide, β-methoxy-ethylimide and γ-methoxy-propylimide, 4- and 5-nitro-1-amino-naphthalene, 2-amino-anthraquinone, 1-amino-4-chloroanthraquinone, 3- or 4-aminodiphenylene oxide, 2-amino-benzthiazole, 2-amino-6-(carboxylic acid methyl ester)-benzthiazole, 2-amino-6-methyl-sulphonyl-benzthiazole, 2-amino-6-cyanobenzthiazole, 2-amino-6-nitro-benzthiazole, 5,6- or 6,7-dichloro-2-amino-benzthiazole, 4-amino-5-bromo-7-nitro-1,2-benzisothiazole, 3-amino-5-nitro-2,1-benzisothiazole, 3-amino-5-nitro-7-bromo-2,1-benzisothiazole, 2-aminothiazole, 2-amino-5-nitrothiazole, 2-amino-4-methylthiazole-5-carboxylic acid ethyl ester, 2-amino-4-methyl-5-acetyl-thiazole, 2-amino-3-cyano-4-methyl-thiophene-5-carboxylic acid . . . ester, 2-phenyl-5-amino-1,3,4-thiadiazole, 3-methylmercapto-5-amino-1,2,4-thiadiazole and 3-β-carbomethoxy-ethylmercapto-5-amino-1,2,4-thiadiazole.

For the preparation of the compounds of the formula I, it is known first to react compounds of the formula II with phosphorus oxychloride in the presence or in the absence of a tertiary amine to give compounds of the general formula III

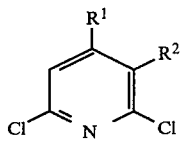

III in which $R^1$ and $R^2$ have the abovementioned meaning (compare J. Org. Chem. 25, 562 (1960), German Offenlegungsschrift No. 2,049,831, German Offenlegungsschrift No. 2,127,521, German Offenlegungsschrift No. 2,814,330, Japanese Pat. No. 39-26,850 and U.S. Pat. No. 2,742,478).

The product prepared by one of these processes is isolated and, if $Z^1$ is not identical to $Z^2$, is reacted, in a first stage, with an amine $Z^1NH_2$.

The reaction is carried out in an inert organic solvent or in an excess of the amine as the solvent. A tertiary amine added to the reaction mixture or an excess of the amine $Z^1NH_2$ serves to trap the hydrogen chloride split off during the reaction. The resulting compounds of the formulae IVa and IVb are then isolated (compare German Offenlegungsschrift No. 2,062,717, German Offenlegungsschrift No. 2,260,827, German Offenlegungsschrift No. 2,605,467, British Pat. No. 1,405,308 and Japanese Pat. No. 77-46,250).

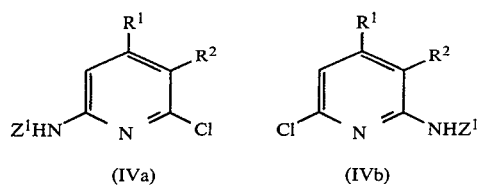

(IVa)   (IVb)

In a second stage, the products of the general formulae IVa and IVb are then reacted with an amine of the formula $Z^2NH_2$ in this amine as the solvent, to give the compounds of the general formula I wherein A is hydrogen, and the end products are isolated.

If $Z^1$ and $Z^2$ are identical, the compounds of the general formula III are reacted with the amine $ZNH_2$, in one process step, in the amine $ZNH_2$ as the solvent, to give the compounds of the formula I wherein A is hydrogen and the end products are isolated (compare German Offenlegungsschrift No. 2,062,717, German Offenlegungsschrift No. 2,260,827, German Offenlegungsschrift No. 2,605,467, British Pat. No. 1,405,308 and Japanese Pat. No. 77-46,250). The synthesis of the dyestuffs of the general formula I wherein A is a radical of the formula —N═N—D is carried out in the customary manner, by coupling diazotised amines of the formula D—$NH_2$ to compounds of the general formula I wherein A is hydrogen, in aqueous mineral acids (compare German Offenlegungsschrift No. 2,156,545, German Auslegeschrift No. 2,211,663, German Offenlegungsschrift No. 2,251,719, German Offenlegungsschrift No. 2,265,458 and German Offenlegungsschrift No. 2,309,658).

This known process involves considerable industrial difficulties and disadvantages, some of which lie in the preparation of the compounds of the formula III, that is to say the 2,6-dichloropyridines, but some of which also lie in the further reaction of these compounds with amines to give the compounds of the formula I, that is to say the 2,6-diaminopyridines. According to the state of the art, in fact, 2,6-dihydroxypyridines are reacted with at least 2 to 3 mols of phosphorus oxychloride for the preparation of the 2,6-dichloropyridines. As can be seen, for example, from Japanese Patent Application No. Sho 39-26,850, page 1, column 2, last paragraph and last but one paragraph, if the molar ratio dihydroxypyridine: phosphorus oxychloride falls below 1:2, this leads to a drastic reduction in the yield of 2,6-dichloropyridine. The excess of phosphorus oxychloride leads, of course, to complications during working up of the reaction batches, since this excess must first be hydrolysed, whilst controlling the temperature and pH value, and since, in this operation, considerable amounts of alkali are consumed and undesired amounts of by-products, in particular phosphates, which must be removed in a satisfactory manner are obtained. An increased processing time and a drastic reduction in the space/time yield are also associated with the considerable volume of liquid thereby obtained.

The isolation and drying of the 2,6-dichloropyridine derivative which follow the hydrolysis of the phosphorus oxychloride necessarily also lead to a certain loss in yield, as does any isolation step, and only methods which are very gentle and thus require technical effort can be applied during drying.

In the known processes, the 2,6-dichloropyridine is reacted with an amine of the formula $Z^1$—$NH_2$ in an anhydrous but water-miscible inert organic solvent. After this reaction, isolation of the resulting monochloro-aminopyridine derivative is also carried out, and the customary losses from working up must in turn be taken into consideration. The resulting product is then reacted in the amine of the formula $Z^2NH_2$ as the solvent, to give the desired compound of the formula I wherein A is hydrogen.

The diaminopyridine derivatives thus obtained must now be separated off from the large excess of amine and isolated. In this case also, the customary losses from working up in turn result. The azo dyestuff of the formula I wherein A denotes a group of the formula D—N=N— can be prepared in the customary manner only after this operation.

However, in the case of this known preparation process, which is carried out in many individual stages with intermediate isolation of the intermediate product in each case, not only must the losses in yield which result in each stage be accepted, but in addition, corresponding amounts of by-products which are to be removed are obtained and, if solvents and excesses of amine are used, losses during recycling of these materials also occur.

Since azo dyestuffs of the formula I wherein A denotes a group of the formula —N=N—D have exceptionally valuable coloristic properties, there was an urgent need to reduce or to avoid the disadvantages and difficulties of the known preparation route.

It has now been found that, contrary to expectations, the reaction of 2,6-dichloropyridine derivatives of the formula III and of analogous 2,6-dibromopyridine derivatives with an amine of the formula $Z^1NH_2$ does not have to be carried out in an anhydrous medium, but that this reaction can also be carried out in the presence of water surprisingly smoothly and without leading to saponification products of the dichloropyridine, and particularly advantageously in a two-phase system of water and an organic solvent which is water-immiscible or miscible with water only to a limited extent.

This surprising knowledge is the key to a new method for the preparation of compounds of the general formula I from 2,6-dihydroxypyridine derivatives of the abovementioned formula II, which is very advantageous from an industrial point of view and can be carried out as a one-pot process.

The present invention thus relates to a process for the preparation of compounds of the general formula I

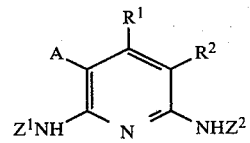

wherein A denotes hydrogen or a radical of the formula —N=N—D, $R^1$ denotes H, alkyl with 1 to 8 C atoms or optionally substituted phenyl, $R^2$ denotes H, cyano, nitro, acyl with 2 to 4 C atoms or sulphomethyl, $Z^1$ and $Z^2$ are identical or different and denote H, optionally substituted alkyl or polyalkoxyalkyl with in each case a total of 1 to 8 C atoms, cycloalkyl with 5 to 7 C atoms, alkenyl with 3 to 5 C atoms or optionally substituted phenyl and D denotes the radical of a customary diazo component of the aromatic or hetero-aromatic series, starting from compounds of the general formula II

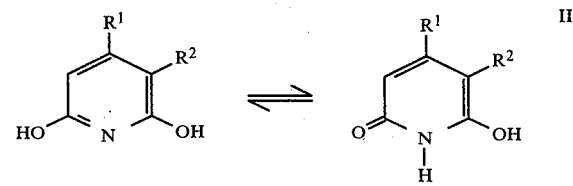

in which $R^1$ and $R^2$ have the abovementioned meanings, by reacting 2,6-dihalogenopyridine derivatives with primary amines to give 2,6-diaminopyridine derivatives and, if appropriate, subsequently coupling these products with diazonium compounds, characterised in that a 2,6-dihalogenopyridine derivative of the formula V

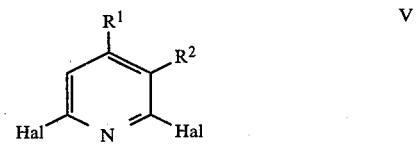

wherein Hal represents chlorine or bromine and $R^1$ and $R^2$ have the abovementioned meanings, is reacted with 1 to 1.1 times the molar amount of an amine of the formula $Z^1NH_2$ in a two-phase system of water and an organic solvent which is insoluble in water or soluble in water only to a limited extent and is inert under the reaction conditions, in the presence of 1 to 1.2 times the molar amount of an inorganic base, at a temperature between 25° and 150° C. and at a pH value of 8 to 13, to give compounds of the general formula VIa and VIb.

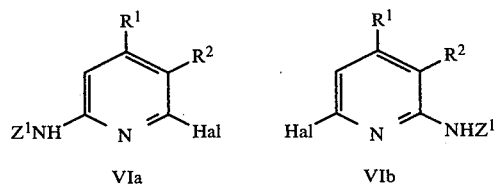

VIa          VIb wherein $R^1$, $R^2$, Hal and $Z^1$ have the abovementioned meanings, and then, after completely separating off the aqueous phase, the resulting batch is reacted with 1 to 1.1 times the molar amount of an amine of the formula $Z^2NH_2$ in the same organic solvent, at temperatures between 80° and 180° C., in the presence of 1 to 1.5 times the molar amount of an inorganic base, to give compounds of the general formula I wherein A is hydrogen, which can optionally be isolated in the customary manner, or, after adjusting the batch to a pH value of 1 to 6 by adding aqueous mineral acid, are coupled with a diazonium compound of the formula

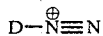

to give an azo dyestuff of the formula I wherein A is a radical of the formula

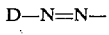

and D has the abovementioned meaning.

Possible organic solvents for carrying out the process according to the invention are alcohols, such as butan-1-ol, butan-2-ol, tert.-butanol, pentan-1-ol, pentan-2-ol, pentan-3-ol, hexan-1-ol, hexan-2-ol and hexan-3-ol, esters, such as acetic acid methyl ester, ethyl ester, n-propyl ester, i-propyl ester, n-butyl ester, i-butyl ester, sec.-butyl ester and i-amyl ester, and substituted aromatics, such as toluene, xylene, chlorobenzene, dichlorobenzene and nitrobenzene.

Inorganic bases which are suitable for the process according to the invention are sodium hydroxide and potassium hydroxide, sodium carbonate and potassium carbonate and sodium bicarbonate and potassium bicarbonate. The reaction of the 2,6-dichloropyridine derivative with the amine of the formula $Z^1$-$NH_2$ in the first process stage is carried out at temperatures between 25° C. and 150° C., preferably at temperatures between 40° and 100° C. The rate of reaction and the isomer ratio of the isomers of the general formula VIa and VIb

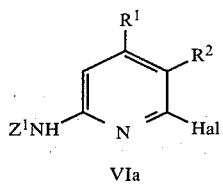 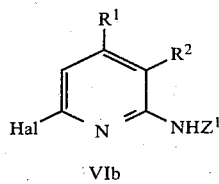

wherein $R^1$, $R^2$, Hal and $Z^1$ have the abovementioned meanings, depend on the reaction temperature. According to experience, the molar ratio of VIa:VIb is between 85:15 and 65:35.

It is expedient to add the organic solvent and the amine $Z^1NH_2$ to a suspension of the compounds of the general formula V and to add the inorganic base at the reaction temperature at a rate such that the pH value of the aqueous phase is always in the range from 8 to 13. The pH value of the aqueous phase should preferably always correspond to the value brought about by the pure amine $Z^1NH_2$ in water.

In a second process stage, the batch obtained in the first stage is reacted, after completely separating off the aqueous phase, but without isolating the intermediate product of the formulae VIa and VIb, with the amine of the formula $Z^2$—$NH_2$ in the same organic solvent, at temperatures between 80° and 180° C., preferably at temperatures between 100° and 170° C.

Preferred organic solvents are thus those which have a boiling point in or above this range and which remain stable and inert during the reaction, such as butanol, pentanol, hexanol, acetic acid butyl ester, acetic acid pentyl ester and the abovementioned substituted aromatics.

The aqueous phase is separated off completely in a manner which is in itself known and which appropriately depends on the nature of the organic solvent used. In the case where aromatics are used, such as toluene, xylene or halogeno-benzenes, that is to say inert solvents which themselves dissolve very little water, the separation can be effected simply by phase separation in a separating funnel. If solvents which take up more water are used, in particular alkanols which are miscible with water to a limited extent, separating off the water is brought to completion by azeotropic distillation.

The inorganic bases serve to trap the hydrogen halide acid liberated during the replacement reaction. They must not react with the solvent, since otherwise side reactions are possible. Thus, for example, in the reaction of a compound of the formula V with the amine $Z^1NH_2$ in butanol in the presence of sodium hydroxide or potassium hydroxide, a butoxy-substituted product is also formed.

If alkanols are used as the solvents, relatively weak or sparingly soluble bases, such as sodium carbonate, potassium carbonate, sodium bicarbonate and potassium bicarbonate, which react exclusively with the hydrogen halide acid, are therefore preferred.

As a rule, 1 equivalent of the inorganic base, relative to 1 mol of a compound of the general formula V, is sufficient per reaction stage. However, the amount of base can be increased up to about 2 equivalents in order to shorten the reaction time.

1 to 1.5 equivalents of the inorganic base are preferably employed.

The reaction times essentially vary between 6 and 36 hours, depending on the reaction temperature and the amine $Z^2NH_2$.

To prepare compounds of the formula I in which $Z^1$ is identical to $Z^2$ and the two radicals can thus be denoted as Z, without indices, the 2,6-dihalogenopyridine derivative of the formula V

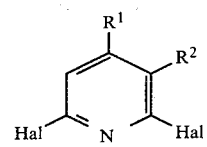

wherein Hal represents chloride or bromine and $R^1$ and $R^2$ have the abovementioned meanings, is reacted with 2 to 2.2 times the molar amount of an amine of the formula $ZNH_2$ in an organic solvent which is insoluble in water or soluble in water only to a limited extent, is optionally saturated with water and is inert under the reaction conditions, at temperatures between 80° and 180° C., in the presence of 2 to 2.5 times the molar amount of an inorganic base, to give a compound of the general formula I wherein A is hydrogen, which can be isolated or further processed, as described above.

The 2,6-dichloropyridine derivatives, that is to say compounds of the formula V in which Hal represents chlorine, are preferably used according to the invention.

If compounds of the formula I wherein A is hydrogen are to be prepared, after the second process stage, these compounds are isolated in a customary manner, for example by stripping off the solvents and the small excesses of amine in vacuo, by steam distillation or by azeotropic distillation, and, if desired, are purified via their salts. As a rule, purification is not necessary, especially if the compounds are to be used for the preparation of dyestuffs.

In contrast, for the preparation of azo dyestuffs of the formula I wherein A is a radical of the formula

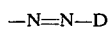

it is even expedient to subject the 2,6-diaminopyridine derivatives prepared according to the invention to further processing directly, without isolation, in a third process stage immediately following their preparation.

In this third stage, aqueous mineral acid is added to the batch obtained in the second stage and the coupling component thus present is coupled in the customary manner by adding a diazo component, and the dyestuff formed is isolated in the customary manner, for example by filtration.

Preferred organic solvents are those which wash impurities in the dyestuff into the filtrate at the filtration temperature, which can be just below the boiling point of the solvent. Such solvents are the abovementioned alcohols, ethers and aromatics.

The coupling reaction is carried out at temperatures of 0° to 40° C. and in a pH range from 1 to 6, preferably between pH 1 and 3.

The use of an inert organic solvent which can easily be regenerated and can be employed uniformly for all the process steps enables the process according to the invention to be carried out in one reaction vessel, that is to say the end product must be isolated only once and the solvent and excesses of amine must be regenerated only once. In contrast, in the processes known hitherto, each intermediate product is isolated, and in each case all the organic constituents must be regenerated.

At the same time, the use of physiologically unacceptable primary amines as solvents becomes superfluous in the process according to the invention. The amount of these primary amines employed is reduced to a minimum by using inorganic bases as trapping agents for the hydrogen halide acid.

The end products of the general formula I wherein A is a radical of the formula —N=N—D are isolated in the simplest manner possible, by filtration. The organic consistituents of the filtrate can be recovered in the pure form by simple steam distillation or by azeotropic or fractional distillation.

Since it is not necessary to use the isolated dried dichloropyridine derivative of the formula III as the starting material in carrying out the process according to the invention, but water-containing suspensions of 2,6-dichloro- or 2,6-dibromo-pyridine derivatives can be employed as the starting material, a further very considerable industrial advantage also results, compared with the known process, which is that it is possible to employ, as the starting material, suspensions of 2,6-dihalogenopyridine derivatives which can be prepared in an industrially simple and elegant manner from 2,6-dihydroxy-pyridine derivatives when these compounds are reacted with phosphorus oxychloride or phosphorus oxybromide in the presence of a basic nitrogen compound, at elevated temperature, the dihydroxypyridine derivatives of the general formula II and phosphorus oxychloride or phosphorus oxybromide being employed in the molar ratio 1:(1 to 1.3), and, after the reaction, excess water is added to the reaction batch to hydrolyse the excess of phosphorus oxyhalide.

0.1 to 1.5 mols, preferably 0.4 to 1.5 mols, of the basic nitrogen compound are usually employed per 1 mol of the dihydroxypyridine of the general formula II. It is usually not necessary to employ more than 1.5 mols of the basic nitrogen compound. Possible basic nitrogen compounds are, above all, tertiary aliphatic or aromatic amines or simple nitrogen-containing heterocyclic compounds, such as, for example, trimethylamine, triethylamine, N-methylpiperidine, N-methylpyrrolidone, pyridine and N,N-dimethyl-m-toluidine. The amines which are insoluble in cold water or only slightly soluble in cold water, such as, for example, isoquinoline, carbazole, acridine, 2-methyl-4-ethyl-pyridine, 2-methyl-5-ethyl-pyridine, 2-methyl-6-ethyl-pyridine, 4-methyl-3-ethyl-pyridine, tri-n-propylamine, tri-n-butylamine, N,N-dimethylaniline and N,N-diethylaniline, are preferred, in particular for economic reasons and on the grounds of less pollution of the environment. Amines which have a moderate solubility in cold water, such as, for example, quinoline, are also preferred if they are volatile in steam. Mixtures of 2 or more basic nitrogen compounds can also be used.

1 to 1.3 mols of phosphorus oxychloride or bromide and 0.1 to 1.5 mols of the basic nitrogen compound, per 1 mol of the starting compound of the general formula II, are mixed with one another and the reaction is carried out, appropriately with stirring, at temperatures of 150° to 250° C., preferably 170° to 220° C. The reflux temperature of the batch in an open system is most simply chosen as the reaction temperature for the reaction according to the invention. Since the amount of phosphorus oxyhalide decreases in the course of the reaction and most of the basic nitrogen compound becomes bonded as the hydrochloride, reaction temperatures of up to 250° C. can be achieved without applying increased pressure. The reaction times vary between 2 and 5 hours, depending on the reaction temperature.

The considerable reduction in the amount of phosphorus oxyhalide compared with conventional processes enables the halogenating agent to be utilised considerably better. Furthermore, working up of the reaction batch is simplified by the reduction in the amount of phosphorus oxyhalide. Whilst after the reaction in the processes known hitherto excess phosphorus oxychloride had to be distilled off or destroyed carefully by adding ice and passed into the effluent as phosphate, in the process according to the invention, working up is preferably effected by a procedure in which cold or, preferably, even hot water is allowed to run into the hot reaction mixture, during which a temperature which is above, preferably 5° to 20° C. above, the melting point of the 2,6-dihalogenopyridine compound of the formula V synthesised is appropriately maintained in the reaction mixture. A suspension of a finely crystalline analytically pure product is immediately obtained in this process and is outstandingly suitable as a starting material for the preparation, according to the invention, of the 2,6-diaminopyridine derivatives of the general formula I.

EXAMPLE 1

150 g of 2,6-dihydroxy-3-cyano-4-methyl-pyridine are added to a solution of 129 g of quinoline and 184 g of phosphorus oxychloride at room temperature. During this addition, the temperature rises to about 65° C. The batch is now heated to 190° C. (internal temperature) in the course of 75 minutes, whilst stirring, and is stirred at this temperature for 3 hours. Thereafter, the batch is allowed to cool to 125° C. (internal temperature), also whilst stirring, and 250 ml of water of 25° C. are added dropwise at this temperature. The batch is cooled to 60° C., 600 ml of n-butanol are added and the batch is neutralised with 360 ml of sodium hydroxide solution of 33° Bé strength. After adding 93.5 g (1.05 mols) of 3-methoxypropylamine, 58 ml of sodium hydroxide solution of 33° Bé strength are added dropwise at 60° C. in the course of 4 hours at a rate such that the pH value of the aqueous phase of the batch is always about 11.

To isolate the reaction product, the salt-containing alkaline aqueous phase is separated off. Using steam, first the n-butanol is subsequently separated out of the batch, which has been rendered acid, and thereafter the batch is rendered neutral and then the quinoline is separated out.

230 g (96% of theory) of a colourless crystalline product of melting point 83°–85° C. remain. This product contains the isomers A and B in the ratio 80:20.

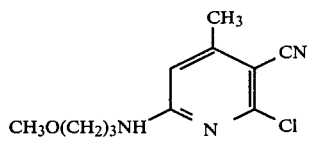  (A)

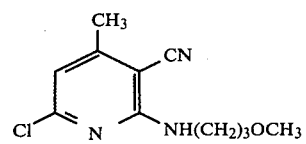  (B)

For further reaction of the product, without intermediate isolation, the aqueous phase of the batch is separated off at 60° C. and the residual water is distilled off azeotropically, the n-butanol passing over with the water being recycled. 106 g (1.05 mols) of n-hexylamine and 53.0 g (0.5 mol) of anhydrous sodium carbonate are then added and the batch is boiled under reflux for 18 hours.

To isolate the reaction product A' and B', the n-butanol and the quinoline are separated off in the above-mentioned manner and the residue is washed with 1 N sodium hydroxide solution and with water. The oil which remains (276.6 g, corresponding to 91% of theory) contains the isomers A' and B' in the ratio 80:20.

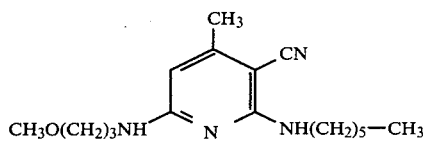  A'

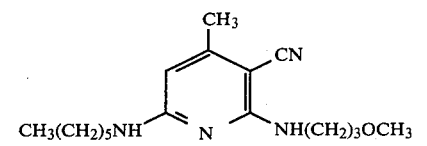  B'

For further reaction of the product, without intermediate isolation, 1,000 ml of water, 1,500 ml of n-butanol and 150 ml of crude hydrochloric acid (d=1.15) are added to the batch, and a diazo solution prepared in the customary manner from 147 g (0.9 mol) of 2-cyano-4-nitroaniline, glacial acetic acid and nitrosyl-sulphuric acid is added dropwise at 0° to 5° C. in the course of ½ hour. The coupling reaction in the batch proceeds immediately. The product is filtered off, washed with 2,000 ml of n-butanol and then with water and dried. 378 g (79% of theory, relative to 2,6-dihydroxypyridine employed) of a red dyestuff which melts at 205°–212° C. and dyes polyester with a clear red shade with a lightfastness of 7 are obtained.

Further dyestuffs from the coupling component (A'+B'):

| Example | Diazo component | Colour shade on polyester |
|---|---|---|
| 1a | 4-nitroaniline | orange |
| 1b | 2-methyl-4-nitroaniline | orange |
| 1c | 2-chloro-4-nitroaniline | scarlet |
| 1d | 2,6-dichloro-4-nitroaniline | scarlet |
| 1e | 2,4-dinitroaniline | red |
| 1f | 2,4-dinitro-6-chloroaniline | red |
| 1g | 2-cyano-4-nitro-6-bromoaniline | red |
|  | Dyestuffs of the following formula 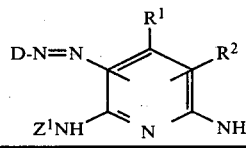 | | can be prepared in an analogous manner.

| Example | D | $R^1$ | $R^2$ | $Z^1$ | $Z^2$ | Shade on polyester |
|---|---|---|---|---|---|---|
| 2 | 4-nitrophenyl | —CH₃ | —CN | CH₃O(CH₂)₃ | HO(CH₂)₂ | orange |
| 3 | 2-cyano-4-nitrophenyl | —CH₃ | —CN | CH₃O(CH₂)₃ | CH₃O(CH₂)₂O(CH₂)₂ | red |
| 4 | 2-chloro-4-nitrophenyl | —CH₃ | —CN | CH₃O(CH₂)₃ | C₆H₅O(CH₂)₃ | scarlet |
| 5 | 4-nitrophenyl | —CH₃ | —CN | H | C₆H₅O(CH₂)₂O(CH₂)₃ | orange |
| 6 | 2-methyl-4-nitrophenyl | —CH₃ | —CN | H | HO(CH₂)₄O(CH₂)₃ | reddish-tinged orange |
| 7 | 2,4-dinitro-6-chlorophenyl | —CH₃ | —CN | H | n-C₄H₉O(CH₂)₃ | red |
| 8 | 2,4-dinitrophenyl | —CH₃ | —CN | HO(CH₂)₃ | (CH₃)₂CHCH₂ | red |
| 9 | 5-nitrothiazol-2-yl | —CH₃ | —CN | HO(CH₂)₂ | C₂H₅O(CH₂)₂ | red-violet |
| 10 | 2-phenyl-1,3,4-thiadiazol-5-yl | " | " | CH₃(CH₂)₃CH(C₂H₅)CH₂ | HO(CH₂)₂ | red |
| 11 | 5-nitrobenzisothiazol-3-yl | —CH₃ | —CN | CH₃(CH₂)₃ | CH₂=CH—CH₂ | violet |
| 12 | 2-cyano-4-nitro-6-chlorophenyl | —CH₃ | —CN | NC—(CH₂)₂ | CH₃COO(CH₂)₃ | red |
| 13 | 4-nitrophenyl | 2-butyl | —CN | HO(CH₂)₂O(CH₂)₂ | —C₆H₅ | orange |
| 14 | 2-methyl-4-(2'-methyl-phenylazo)-phenyl | 2-ethylhexyl | —CN | H | C₆H₅—CHOHCH₂ | red |
| 15 | 6-methoxy-benzthiazol-2-yl | —CH₃ | —NO₂ | C₂H₅O(CH₂)₃ | n-C₄H₉O(CH₂)₃ | violet |
| 16 | 2-chloro-6-methylphenyl | —C₂H₅ | CH₃CO— | HO(CH₂)₂ | NC(CH₂)₂O(CH₂)₄ | yellowish-tinged orange |
| 17 | 2-cyano-4-nitro-6-bromophenyl | —CH₃ | C₃H₇CO— | H | cyclohexyl | red |
| 18 | 4-benzoylphenyl | —CH₃ | CH₃SO₂— | CH₃O(CH₂)₃ | —C₅H₁₁ | orange |

EXAMPLE 19

2,6-Dichloro-3-cyano-4-methyl-pyridine is prepared from 150 g of 2,6-dihydroxy-3-cyano-4-methyl-pyridine, 184 g of phosphorus oxychloride and 123 g of quinoline and hydrolysed, in the manner described in Example 1. 500 ml of chlorobenzene are added to the cooled batch, and the batch is neutralised with sodium hydroxide solution of 33° Bé strength. The aqueous phase is separated off in a separating funnel. 117 g of anhydrous sodium carbonate and 130 g of ethanolamine are now added to the organic phase and the batch is boiled under reflux for 12 hours. It is then allowed to cool to room temperature and washed with water and the chlorobenzene is distilled off. The oil which remains has the following chemical structure

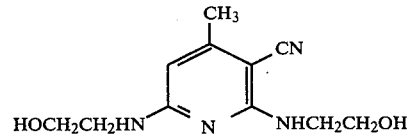

It couples with diazotised 4-nitroaniline to give a dyestuff which has an absorption maximum, when dissolved in phthalic acid diethyl ester, of 490 mm, melts at 264°–70° C. and dyes polyester reddish-tinged orange.

Dyestuffs of the following formula

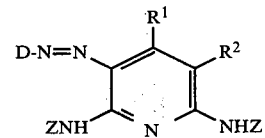

can be prepared in an analogous manner.

| Example | D | $R^1$ | $R^2$ | Z | Shade on polyester |
|---|---|---|---|---|---|
| 20 | 4-nitrophenyl | —CH₃ | —CN | CH₃O(CH₂)₃ | orange |
| 21 | 2-bromo-4-nitrophenyl | —CH₃ | —CN | C₆H₅—O(CH₂)₂O(CH₂)₃ | scarlet |
| 22 | 4-ethoxycarbonylphenyl | —C₂H₅ | —CN | CH₃(CH₂)₇ | orange |
| 23 | 2-cyano-4-nitrophenyl | —CH₃ | —NO₂ | HO(CH₂)₄O(CH₂)₂ | red |
| 24 | 2,4-dinitrophenyl | —C₂H₅ | —NO₂ | NC(CH₂)₂O(CH₂)₂ | red |
| 25 | 4-phenylazophenyl | -n-C₅H₁₁ | —NO₂ | (C₂H₅)₂N(CH₂)₂ | orange |
| 26 | benzthiazol-2-yl | —CH₃ | C₂H₅CO— | C₆H₅COO(CH₂)₂ | yellowish-tinged red |
| 27 | 2,4-dinitro-6- | —CH₃ | —SO₂CH₃ | NO(CH₂)₂OC₆H₄ | red |

| Ex-ample | D | $R^1$ | $R^2$ | Z | Shade on polyester |
|---|---|---|---|---|---|
| | bromoaniline | | | | |

We claim:
1. In the process for preparation of 2,6-diaminopyridines of the formula

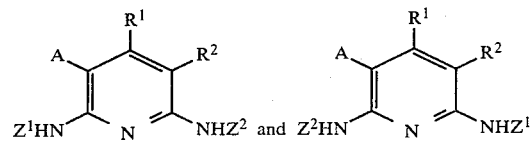 and wherein
A is hydrogen or —N=N—D;
$R^1$ is H, alkyl having 1 to 8 carbon atoms, phenyl or phenyl substituted by halogen, alkyl having 1 to 8 carbon atoms or alkyl having 1 to 8 carbon atoms;
$R^2$ is H, cyano, nitro, alkanoyl having 2 to 4 carbon atoms or methylsulphonyl;
$Z_1$ and $Z_2$ are identical or different and each is H, alkyl having 1 to 8 carbon atoms, polyalkoxyalkyl having 1 to 8 carbon atoms, cycloalkyl having 5 to 7 carbon atoms, alkenyl having 3 to 5 carbon atoms, or phenyl, said alkyl and polyalkoxyalkyl being unsubstituted or substituted by hydroxyl, alkoxy having 1 to 4 carbon atoms, alkenyloxy having 3 to 5 carbon atoms, cycloalkyloxy having 5 to 7 carbon atoms, phenoxy, phenylalkoxy, alkanoyloxy having 1 to 4 carbon atoms, cyano, amino, alkylamino or dialkyl amino having 2 to 8 carbon atoms and said phenyl being unsubstituted or substituted by alkyl having 1 to 4 carbon atoms, halogen or hydroxyethoxy; and
D is a customary diazo coupled moiety of the benzene, azobenzene, benzophenone, diphenyl sulphone, thiazole, isothiazole, benzthiazole, benzisothiazole or thiadiazole series;
said process comprising reacting a 2,6-dihalopyridine of the formula

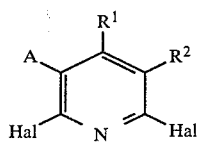

wherein Hal is chlorine or bromine, with a primary amine and when A is —N=ND subsequently coupling the product with a diazonium compound,
wherein the improvement comprises reacting the 2,6-dihalopyridine with 1 to 1.1 times the molar amount of an amine of the formula $Z^1NH_2$ in a two-phase system of water and an organic solvent which is insoluble in water or soluble in water only to a limited extent and which is inert under the reaction conditions, in the presence of 1 to 1.2 times the molar amount of an inorganic base, at a temperature between 25° and 150° C. and at a pH of 8 to 13, to produce compounds of the formula

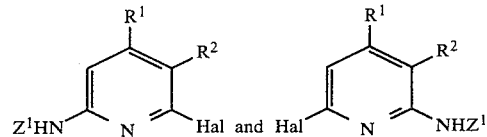

and then, after completely separating off the aqueous phase, the resulting mixture is reacted with 1 to 1.1 times the molar amount of an amine of the formula $Z^2NH_2$ in the same organic solvent, at temperatures between 80° and 180° C., in the presence of 1 to 1.5 times the molar amount of an inorganic base, to produce 2,6-diaminopyridine compounds of the formula

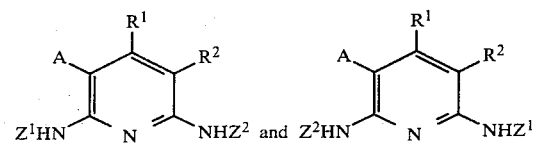

where A is H; and when A is —N=ND, adding an aqueous mineral acid to the reaction mixture to adjust the mixture pH to 1 to 6 and then coupling the 2,6-diaminopyridines with a diazonium compound of the formula

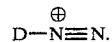

2. The process according to claim 1, wherein the reaction with the amine of the formula $NH_2Z^1$ is carried out at temperatures of 40° to 100° C. and the reaction with the amine of the formula $NH_2Z^2$ is carried out at temperatures of 100° to 170° C.

3. In the process according to claim 1 wherein said 2,6-dihalopyridine is used in the form of an aqueous suspension or paste which has been obtained by reacting a starting pyridine compound of the formula

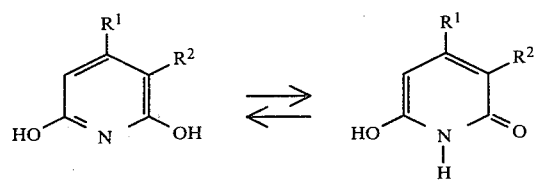

with phosphorus oxyhalide in the presence of a basic nitrogen compound, at elevated temperature wherein the additional improvement comprises using 1 to 1.3 mols of phosphorus oxyhalide per 1 mol of said starting pyridine and, after the reaction, adding excess water to the reaction mixture to hydrolyse the excess phosphorus oxyhalide.

4. The process according to claim 3, wherein said basic nitrogen compound is sparingly soluble in water or is volatile in steam.

5. The process according to claim 4, wherein said basic nitrogen compound is quinoline, isoquinoline, carbazole, acridine, ethyl-methyl-pyridine, tri-n-propylamine or tri-n-butylamine.

6. The process according to claim 3 wherein said excess water is added into the still hot reaction mixture.

7. In the process for preparation of 2,6-diaminopyridines of the formula

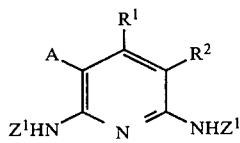

wherein

A is hydrogen or —N=N—D;

R$^1$ is H, alkyl having 1 to 8 carbon atoms, phenyl or phenyl substituted by halogen, or alkyl having 1 to 8 carbon atoms;

R$^2$ is H, cyano, nitro, alkanoyl having 2 to 4 carbon atoms or methylsulphonyl;

Z$^1$ is H, alkyl having 1 to 8 carbon atoms, polyalkoxyalkyl having 1 to 8 carbon atoms, cycloalkyl having 5 to 7 carbon atoms, alkenyl having 3 to 5 carbon atoms, or phenyl, said alkyl and polyalkoxyalkyl being unsubstituted or substituted by hydroxyl, alkoxy having 1 to 4 carbon atoms, alkenyloxy having 3 to 5 carbon atoms, cycloalkyloxy having 5 to 7 carbon atoms, phenoxy, phenylalkoxy, alkanoyloxy having 1 to 4 carbon atoms, cyano, amino, alkylamino or dialkyl amino having 2 to 8 carbon atoms and said phenyl being unsubstituted or substituted by alkyl having 1 to 4 carbon atoms, halogen or hydroxyethoxy; and D is a customary diazo coupled moiety of the benzene, azobenzene, benzophenone, diphenyl sulphone, thiazole, isothiazole, benzthiazole, benzisothiazole or thiadiazole series;

said process comprising reacting a 2,6-dihalopyridine of the formula

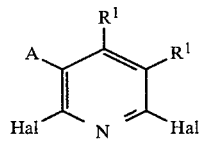

wherein Hal is chlorine or bromine, with a primary amine and when A is —N=ND subsequently coupling the product with a diazonium compound, wherein the improvement comprises reacting the starting pyridine compound of the formula

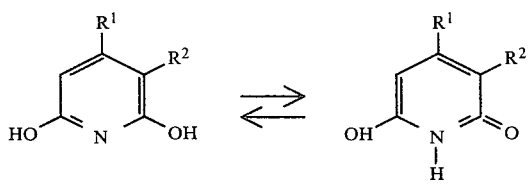

with phosphorus oxyhalide in the presence of a basic nitrogen compound at elevated temperature wherein the additional improvement comprises using 1 to 1.3 mols of phosphorus oxyhalide per 1 mol of said starting pyridine and, after the reaction, adding excess water to the reaction mixture to hydrolyze the excess phosphorus oxyhalide, adding an organic solvent which is insoluble in water or soluble in water to a limited extent, and which is inert under the reaction conditions, and reacting the compound

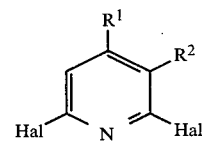

contained in the organic phase with 2 to 2.2 times the molar amount of an amine of the formula Z$^1$NH$_2$ at temperatures between 80° and 180° C., in the presence of 2 to 2.5 times the molar amount of an inorganic base, separating off the organic phase, and when A is —N=ND, adding an aqueous mineral acid to the product obtained to adjust the mixture pH to 1 to 6 and then coupling the 2,6-diaminopyridine with a diazonium compound of the formula

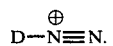

* * * * *